United States Patent [19]
Kenley et al.

[11] Patent Number: 6,153,102
[45] Date of Patent: Nov. 28, 2000

[54] DISINFECTION OF DEAD-ENDED LINES IN MEDICAL INSTRUMENTS

[75] Inventors: Rodney S. Kenley, Libertyville; Derek Wiebenson, Palatine, both of Ill.

[73] Assignee: Aksys, Ltd., Lincolnshire, Ill.

[21] Appl. No.: 09/236,764

[22] Filed: Jan. 25, 1999

Related U.S. Application Data

[60] Continuation-in-part of application No. 08/929,943, Sep. 15, 1997, Pat. No. 5,863,421, which is a division of application No. 08/560,439, Nov. 17, 1995, Pat. No. 5,702,606, which is a division of application No. 08/388,275, Feb. 13, 1995, Pat. No. 5,591,344.

[51] Int. Cl.$^7$ ................ A61L 2/00; A61L 2/16; A61L 2/18
[52] U.S. Cl. .............. 210/636; 210/764; 422/1; 422/28; 422/38
[58] Field of Search ........................ 210/636, 645, 210/646, 748, 764; 422/1, 26, 28, 38

[56] References Cited

U.S. PATENT DOCUMENTS

| | | | |
|---|---|---|---|
| 3,744,636 | 7/1973 | Commarmot | 210/180 |
| 4,166,031 | 8/1979 | Hardy | 210/96.2 |
| 4,399,030 | 8/1983 | Hlavinka et al. | 210/91 |
| 4,444,596 | 4/1984 | Gortz et al. | 210/90 |
| 4,695,385 | 9/1987 | Boag | 210/636 |
| 4,789,467 | 12/1988 | Lindsay et al. | 210/103 |
| 5,304,349 | 4/1994 | Polaschegg | 422/101 |
| 5,492,672 | 2/1996 | Childers et al. | 422/28 |
| 5,527,508 | 6/1996 | Childers et al. | 422/28 |
| 5,591,344 | 1/1997 | Kenley et al. | 210/636 |
| 5,788,925 | 8/1998 | Pai et al. | 422/3 |
| 5,879,328 | 3/1999 | Holmberg et al. | 604/82 |

*Primary Examiner*—John Kim
*Attorney, Agent, or Firm*—McDonnell Boehnen Hulbert & Berghoff

[57] ABSTRACT

A method of disinfection of a dead-ended fluid line in a medical instrument such as a dialysis machine is described. The method comprises introducing a heated fluid into the fluid line, allowing the fluid to remain in the line for an experimentally determined optimal dwell period, removing the fluid from the fluid line, and then repeating the cycle for a time period sufficient to achieve a disinfection of the fluid line. The optimum dwell period and frequency for exchanging the heated fluid is determined so that the heated fluid is left resident in the line to exert a cidal effect but not so long that the it cools to the point of being ineffective, nor changed so frequently that that the time spent with no hot water resident in the line begins to detract (e.g., unduly prolong) the disinfection process. A representative cycle is introducing water at a temperature of about 85 degrees C, allowing it to reside in the fluid line for about 10 seconds, withdrawing the water, and then reintroducing water at 85 degrees C. The process continues for 1–2 hours. Variation from the representative cycle will be expected based on parameters such as the degree to which disinfection is to be achieved, the length and diameter of the fluid line, the temperature of the fluid, the ambient temperature, the presence of elements in the fluid line that contribute to heat loss, the material used for fluid line tubing, and whether the fluid comprises water or a disinfection solution such as a dilute citric acid solution. The optimum dwell period and frequency of the cycles can be determined experimentally from the teachings described herein.

25 Claims, 7 Drawing Sheets

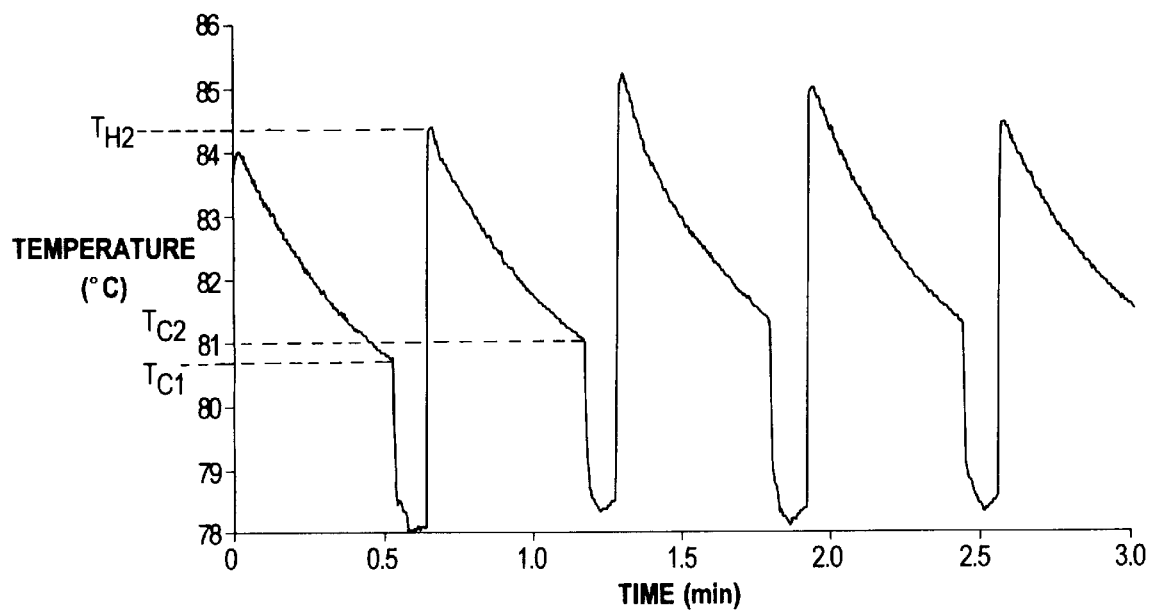

DISINFECTION OF DEAD-ENDED LINES IN MEDICAL INSTRUMENTS

CROSS-REFERENCE TO RELATED APPLICATIONS

This is a continuation-in-part of Ser. No. 08/929,943, filed Sep. 15, 1997, now U.S. Pat. No. 5,863,421, which is a division of Ser. No. 08/560,439 filed Nov. 17, 1995, now U.S. Pat. No. 5,702,606, which is a division of Ser. No. 08/388,275 filed Feb. 13, 1995, now U.S. Pat. No. 5,591,344, the entire contents of which are incorporated by reference herein.

BACKGROUND OF THE INVENTION

1. Field of the Invention

This invention relates generally to the field of medical instruments such as dialysis machines, and more particularly to the process of disinfection of such instruments. Even more particularly, the invention relates to a method for disinfecting a line that is dead-ended in a medical instrument.

2. Description of Related Art

Dialysis machines are machines that are used for treating patients suffering from inadequate kidney function. The machines typically have an extracorporeal blood circulation circuit that withdraws blood from the patient into an arterial line, circulates the blood to a dialyzer filter, and then returns the blood back to the patient via a venous line. The dialyzer filter is a semi-permeable membrane that separates the patient's blood from a dialysate solution that is circulated on the other side of the membrane. Blood-borne toxins and excess water are removed from the patient's blood though the membrane and are carried away in the dialysate solution.

The extracorporeal circuit typically includes a blood pump that is used to pump the patient's blood through the arterial line, dialyzer and back to the patient via the venous line. A venous bubble trap is typically placed in the venous line, for the purpose of separating out any bubbles that may have formed in the blood. In most machines, the venous bubble trap includes a vent line connected to atmosphere. An air pump is also typically placed in the vent line. Operation of the air pump in either the forward or reverse direction changes the pressure in the venous bubble trap, thereby raising or lowering the blood level in the venous bubble trap.

After the end of the dialysis treatment, the entire machine is subject to a cleaning and disinfection process. In the situation where the blood tubing set, dialyzer and other fluid pathways in the extracorporeal circuit are reused instead of replaced, then of course the extracorporeal circuit must be cleaned and disinfected. Methods of achieving a high level disinfection of a dialysis machine, including the extracorporeal circuit thereof, are described in the patent to Rodney S. Kenley et al., U.S. Pat. No. 5,591,344, assigned to the assignee of the present invention Aksys, Ltd., the entire contents of which are incorporated by reference herein. Additional methods and procedures for hot water disinfection are claimed in U.S. Pat. No. 5,651,893, also awarded to Rodney S. Kenley et al., and assigned to Aksys Ltd.

When a fluid line that is to be disinfected comprises a tube through which water (or a solution containing disinfection chemicals) can be continuously circulated, achieving a required level of disinfection is relatively straight forward. For example, in a hot water disinfection process, heated water at a predetermined temperature is allowed to flow through the tube for a predetermined amount of time, such as circulation of water at 80 degrees C for one hour.

A particular fluid path in a medical instrument, such as a dialysis machine, may be designed such that fluids cannot flow through a tube segment, that is, in one end of the segment and out the other end. In the known prior art, achieving disinfection of such a fluid line has been problematical at best, and such "dead-ended" fluid lines have generally been avoided. For example, if chemical disinfection agents are used then there is a problem of adequately rinsing the fluid segment and removing all of the chemical agents. If hot water techniques are used, there is no way to flow water through the tube segment and maintain a constant high level disinfection temperature in the fluid segment.

The present invention overcomes these problems and provides methods and techniques for achieving disinfection of a "dead-ended" fluid path or line. The methods and techniques can be applied to a clean and rinse process, in addition to a disinfection process.

SUMMARY OF THE INVENTION

A method is provided for achieving disinfection of a dead-ended fluid line in a medical instrument such as a dialysis machine. The method comprises the steps of (a) introducing a heated fluid into the fluid line, (b) allowing the fluid to remain in the line for an experimentally determined optimum dwell period, during which the fluid cools, (c) removing the fluid from the fluid line, and then repeating steps (a)–(c) in a series of cycles for a time period sufficient to achieve a disinfection of the fluid line.

The optimum dwell period and frequency for exchanging the heated fluid is determined so that the fluid is left resident in the line to exert a cidal effect therein, but not so long that it cools to the point of being ineffective, nor changed so frequently that that the time spent with no hot water resident in the line begins to detract from the disinfection process (e.g., unduly prolong it or reduce the average temperature in the line below a satisfactory level). Preferably the heated fluid comprises a physiologically safe solution such as a dilute citric acid solution, or it can simply be heated water.

A representative cycle is introducing water into the line having a temperature of about 85 degrees C, allowing it to reside in the fluid line for about 5–10 seconds, withdrawing the water, and then repeating the process over and over again, i.e., reintroducing water at 85 degrees C into the line, allowing it to dwell for 5–10 seconds, withdrawing the water, an so on. The process continues for 1–2 hours.

To achieve satisfactory disinfection in any given dead ended line in a medical instrument, some variation from the representative cycle described above can be expected. The variation is based on parameters such as the length and diameter of the fluid line, the temperature of the fluid, the ambient temperature, the presence of elements in the fluid line that contribute to heat loss, the material used for fluid line tubing, and whether the fluid comprises water or a disinfection solution such as a dilute citric acid solution. The optimum frequency can be determined experimentally from the teachings described herein.

The concept of introducing fluid into the dead-ended line, allowing it to reside for a dwell period, removing it, and repeating the process in a series of cycles can be used as a cleaning and rinse process, in addition to disinfection. Thus, a method of cleaning and rinsing a dead-ended fluid line in a medical instrument is provided, comprising the steps of filling the fluid line with a fluid, allowing the fluid to remain in said fluid line for a dwell time δ, removing the fluid from the fluid line after said dwell time δ has elapsed, and repeating the process in a series of cycles for a time period sufficient to achieve a cleaning and rinsing of the fluid line. The fluid used for cleaning and rinsing could be water, a dialysate solution, a chemical cleaning and disinfection fluid, citric acid solution, or other suitable fluid, and need not be heated. Additionally, the dwell time δ for cleaning and rinsing cycles may be different, e.g., shorter than that used for disinfection, and may be 0 (removal commencing as soon as the dead-enclosed line is filled).

BRIEF DESCRIPTION OF THE DRAWINGS

In the following detailed description, reference will be made to the appended drawing figures, in which like reference numerals refer to like elements in the various views, and in which:

FIGS. 3–9 are graphs of the temperature in the venous line of FIG. 2 as a function of time for many cycles of operation of the method, with each of FIGS. 3–9 having a different dwell time for the heated fluid, with the dwell time and cycles shown in the graph of FIG. 6 being considered optimal for the vent line of FIG. 2;

FIG. 10 is a table of the average temperature present in the vent line of FIG. 2 for the seven different dwell times and the cycles of FIGS. 3–9, indicating that the dwell time of 10 seconds in the graph of FIG. 6 achieved the highest average temperature during the disinfection period.

DETAILED DESCRIPTION OF THE PREFERRED EMBODIMENT OF THE INVENTION

Figure 1:
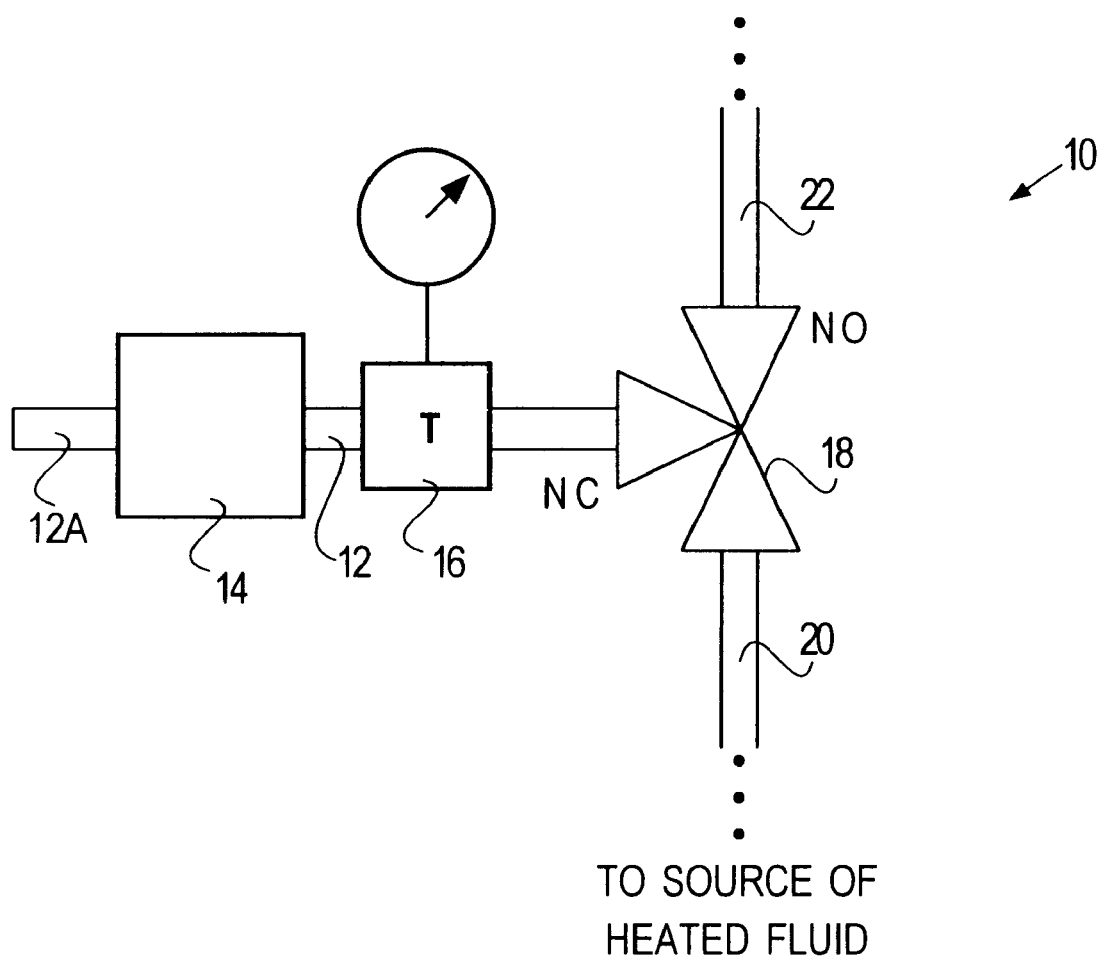
FIG. 1 is an illustration of a representative dead-ended line in a medical instrument.

Referring now to FIG. 1, a representative medical instrument 10, such as a dialysis machine (the details and type of which are not important) includes a dead-ended line 12 terminating in pressure transducer isolator, or any other piece of equipment 14, the details of which are not important. The line 12 is considered "dead ended" because although water or other fluid can flow into the line 12, it is not in a loop or circuit such that fluid can flow in one end and out the other. The fluid can be introduced or withdrawn from the line 12 by using positive pressure and pumping the fluid into the line 12 via a line 20 and operating a valve 18 such that the normally closed port NC is opened. Fluid is withdrawn from line 12 by creating negative pressure or vacuum in line 20 with port NC of valve 18 open. Alternatively, pressure adjustment apparatus (such as a pump) could be placed behind the element 14 in line 12A. The pump would draw fluid from the line 20 into the line 12 with negative pressure and expel the fluid from the line 12 using positive pressure.

The fluid line 12 may include various hydraulic devices or elements, or instruments for monitoring conditions in the line 12, such as a thermistor 16. Furthermore, the line 12 may be of any suitable length, although the shorter the line is between the valve 18 and the terminus of the line 12 at element 14 the better. This is because the time it takes to introduce and remove heated fluids from the line 12 should be minimized so as to avoid cooling of the line 12 and components therein below a suitable disinfection temperature, and thus allow the heated fluid to have a maximum cidal effect.

The principle of operation of the invention is as follows. At some point during the operation of the medical instrument 10, the instrument will need to be subject to a cleaning and disinfection process. After the fluid circuits have been flushed and cleaned (including the dead ended line using the cyclic process described herein), the disinfection process begins. Fluid is heated within the instrument 10 (or supplied from an outside source) and then circulated throughout the fluid passages in the machine for a length of time and at a temperature $T_H$ sufficient to achieve a required disinfection of the machine. An example would be circulating water heated to 85 degrees C throughout the machine for a period of one hour.

During this period of disinfection, the dead-ended line 12 must also be disinfected. To achieve disinfection of line 12, the line 12 is filled with fluid heated to the high level disinfection temperature $T_H$. The heated fluid in line 20 is diverted into the line 12 by opening the normally closed port NC of the valve 18, and pumping or otherwise drawing the fluid into the line 12 such that it fills the line.

The fluid at temperature $T_H$ is allowed to remain in the fluid line 12 for an experimentally determined optimum dwell time δ, during which the temperature of the fluid decreases from $T_H$ to a cooler temperature $T_C$. The heat loss, and thus optimum dwell time, is dependent upon factors such as the length and diameter of the line, the presence of heat-conducting equipment in the line, the difference between the temperature of the fluid and the ambient temperature, the coefficient of heat transfer of the tubing constituting line 12, the amount of time it takes to flush and fill the line 12, and still other factors. The optimum dwell time δ may, for example be less than 20 seconds. A dwell time δ of between 5 and 15 seconds may be suitable for many applications. A preferred method of experimentally determining the optimum dwell time is explained further below.

After the dwell period δ has elapsed, the fluid is removed from the line 12. For example, the valve 18 is opened and the fluid is removed by negative pressure into line 20 or into line 22, perhaps with an assist by a pump in segment 12A. Preferably, the removal of the cooled fluid in the line 12 is achieved as quickly as possible.

The steps of introducing the heated fluid, allowing it to remain in the fluid line, and removing are repeated in a series of cycles for a time period sufficient to achieve the required level of disinfection of the fluid line. For example, the cycles may continue for one hour. This period should coincide with the disinfection period for the remainder of the machine 10.

In one embodiment, the fluid used for high level disinfection comprises water heated to a high level disinfection temperature. This temperature $T_H$ is a function of the disinfection time, with the higher the temperature the shorter the total disinfection time, the lower the temperature the longer the disinfection time. Further, the temperature $T_H$ will depend on the level of disinfection that is specified for the machine (usually determined by industry standards bodies or government regulations). For example, the temperature may be between 80 and 87 degrees C.

In another embodiment, the entire machine, including the line 12, is disinfected with a dilute citric acid solution. The temperature $T_H$ of the fluid may be able to be somewhat less with a citric acid solution, since the citric acid provides some cidal effect of its own.

In another aspect of the invention, the medical instrument 10 may comprise a dialysis machine. The dialysis machine comprises an extracorporeal blood circuit, and the dead-ended fluid line 12 comprises a vent line in a bubble trap in the extracorporeal circuit. This embodiment is described in further detail below in the context of FIGS. 2–11.

Figure 2:
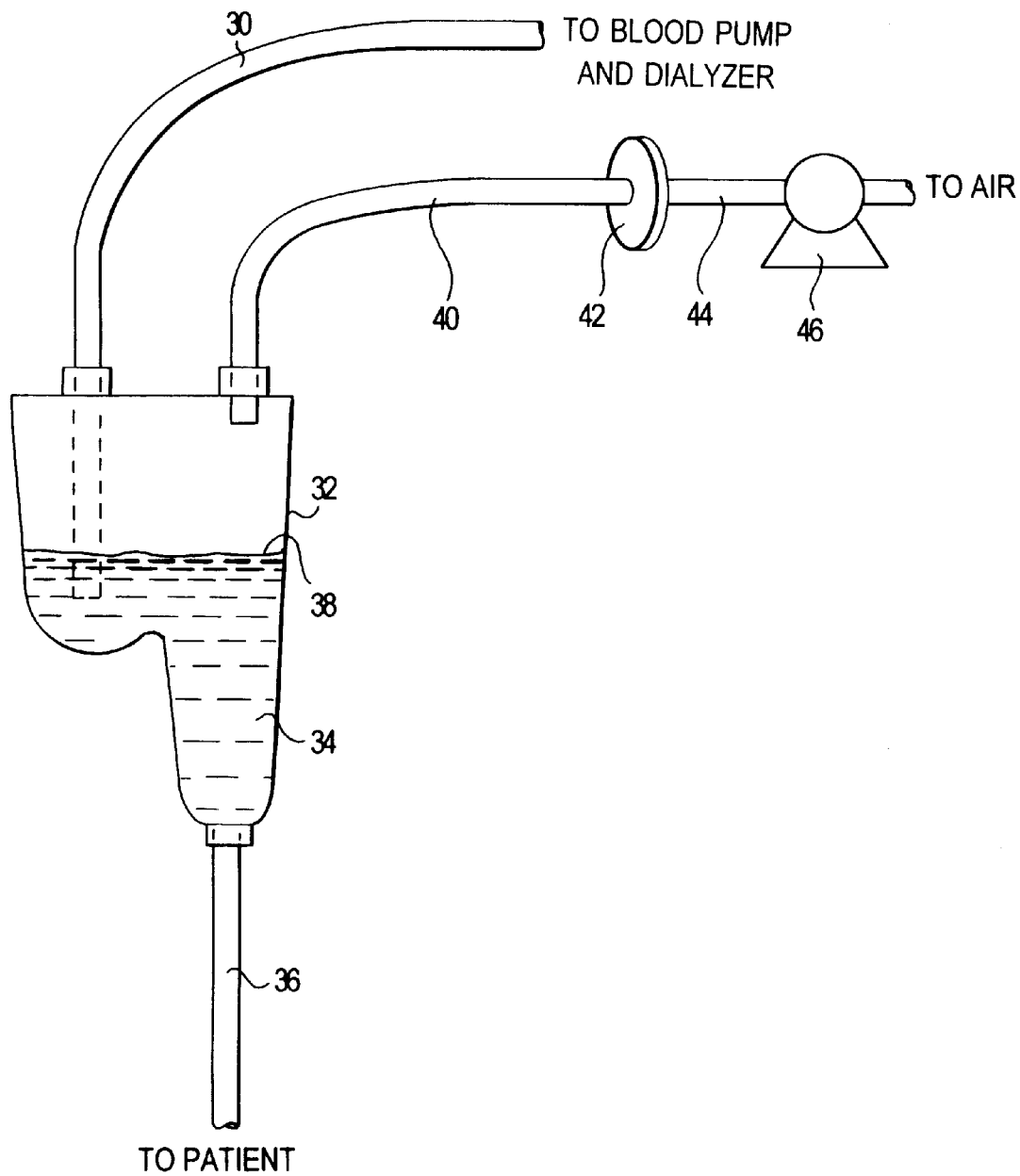
FIG. 2 is an illustration of a portion of a venous line of an extracorporeal circuit of a dialysis machine, showing a venous bubble trap therein having a dead-ended vent line.

Referring now to FIG. 2, a portion of an extracorporal blood circuit of a kidney dialysis machine is shown. The details of the extracorporeal circuit are not particularly important, and may be as described in the above-referenced patents issued to Rodney S. Kenley et al., or otherwise. The extracorporeal circuit includes a venous line 30 that is connected to a dialyzer filter and a blood pump (not shown). During dialysis, blood flows from the patient, through the blood pump and dialyzer and into the venous line 30. The blood is introduced into a venous drip chamber or bubble trap 32. The bubble trap 32 contains a quantity of blood 34. The blood is withdrawn from the bubble trap 32 at the bottom thereof and returned to the patient via a line 36 which terminates in a venous fistula needle (not shown) that is inserted into the patient's circulatory system.

During the dialysis treatment, the level of blood 38 in the bubble trap 32 should be maintained at a desired level. If the level is too low, excessive foaming of the blood occurs in the bubble trap 32. To adjust the level, it is known in the art to adjust the pressure in the bubble trap. In the embodiment of FIG. 2, the pressure is adjusted by means of a vent line 40. The vent line 40 is a dead-ended line, in that it terminates in a pressure transducer isolator 42 comprising a disc-shaped membrane that is impervious to fluids and is permeable to air. The back side of the isolator 44 is connected to a pump 46. Operation of the pump 46 in either the forward or reverse direction causes air to be injected into or removed from the line 40, thereby increasing or decreasing, respectively, the pressure and hence blood level 38 in the bubble trap 32.

In a preferred embodiment, the extracorporeal circuit containing the venous line 30, bubble trap 32, vent line 40 and line 36 is reused and disinfected after each treatment. A preferred method is using hot water (or a heated dilute citric acid solution), as described and claimed in U.S. Pat. Nos. 5,591,344 and 5,651,893, both owned by Aksys Ltd., the assignee of the present invention.

To disinfect the line 30, the process is similar to that described in conjunction with FIG. 1. Water heated to a high level disinfection temperature $T_H$ is continuously circulated through the venous line 30 and the segment 36 for one hour. (The line 36 is connected by the patient to a disinfection manifold port in the machine after the treatment has ended, as described in detail in the above-referenced patents). The water fills the bubble trap 32. The heated fluid in line 20 is drawn into the vent line 40 by operation of the pump 46 in the reverse direction, thereby drawing the hot water into the line 40 such that it fills the line and makes contact with the surface of the pressure transducer isolator 42.

The fluid at initial temperature $T_H$ (e.g., 85 degrees C) is allowed to remain in the line 40 for an experimentally determined optimum dwell time δ, during which the temperature of the fluid decreases from $T_H$ to a cooler temperature $T_C$. The heat loss, and thus optimum dwell time, is dependent upon the several factors indicated above. In the illustrated embodiment, the optimum dwell time is between 5 and 15 seconds, with 10 seconds being considered ideal.

After the dwell period 6 has elapsed, the fluid is removed from the line 40. In the embodiment of FIG. 2, the pump 46 operates in the forward direction to expel the fluid into the drip chamber 32 using positive pressure. Preferably, the removal of the cooled fluid in the line 40 is achieved as quickly as possible. Since fluid is continuously being circulated through the bubble trap, the bubble trap is maintained essentially continuously at a steady state of temperature $T_H$.

The cycle is then repeated. The pump 46 draws a new quantity of water at temperature $T_H$ into the line 40, it remains there for a period of approximately 10 seconds, and then is expelled, a new quantity of hot water is drawn into the line, and so on. For example, the cycles may continue for one hour. This period should coincide with the disinfection period for the remainder of the extracorporeal circuit, or may be longer depending on the average disinfection temperature present in the line 40 during the disinfection period.

FIGS. 3–9 are graphs of temperature measured in the line 40 as a function of time during several cycles of operation, with each figure having a different dwell period. The graphs were generated as part of an experiment to determine the optimum dwell period δ. The optimum period can be obtained in several ways, such as the dwell having the highest average temperature in the line 40, the dwell in which the difference between the high temperature $T_H$ and the cooler temperature $T_C$ is minimized, or the dwell period in which the average temperature of the coolest temperature $T_C$ is a maximum.

Figure 3:
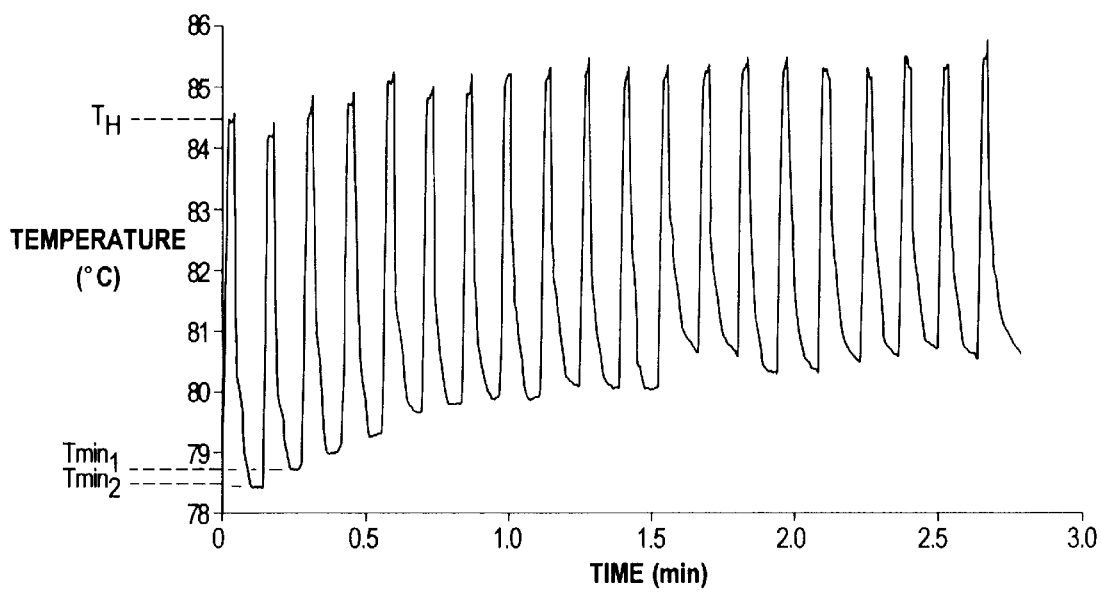

In FIG. 3, the dwell time is zero, meaning that as soon as the water has filled the line 40 the water is withdrawn. The high temperature $T_H$ for the cycles is approximately 84–86 degrees C. The minimum temperature $T_{min}$ starts out at approximately 78.5 C. degrees for the first cycle ($T_{min1}$), but increases gradually to a steady state of a little under 81 degrees C.

Figure 4:
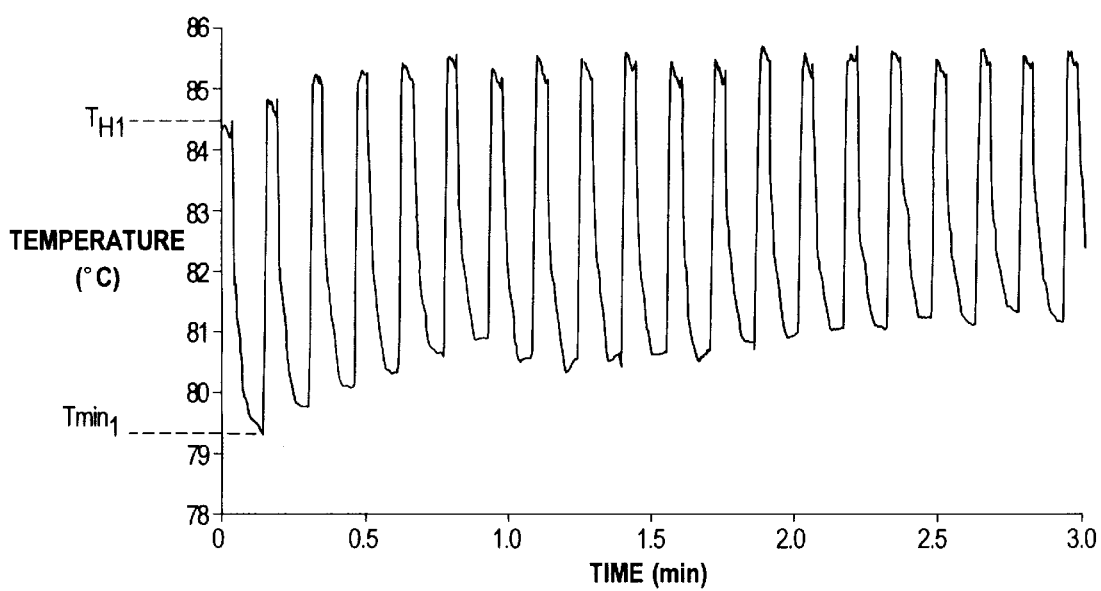

In FIG. 4, the dwell period is one second. In both FIGS. 1 and 2, note the extremely rapid drop-off in temperature from $T_H$ when the withdrawal of fluid commences. Note also in FIG. 4 that the average temperature of the minimum temperature $T_{min}$ is slightly higher than in FIG. 3, reaching a steady state of a little over 81 degrees C after about 2 minutes.

Figure 5:
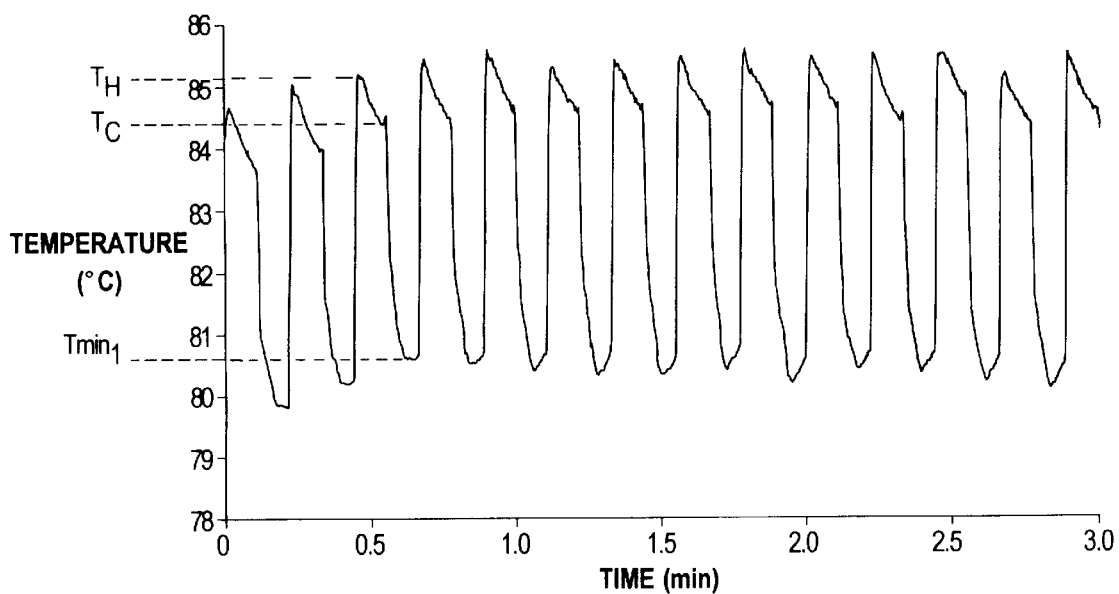

In FIG. 5, the dwell time is 5 seconds. The temperature in the line exhibits an exponential decay as indicated at 50 down to $T_C$, followed by a sharp drop in temperature down to $T_{min}$ as indicated at 52. The longer dwell time means a higher average temperature in the line 40, but a cooler minimum temperature $T_{min}$ as compared to the 1 second dwell in FIG. 4.

Figure 6:
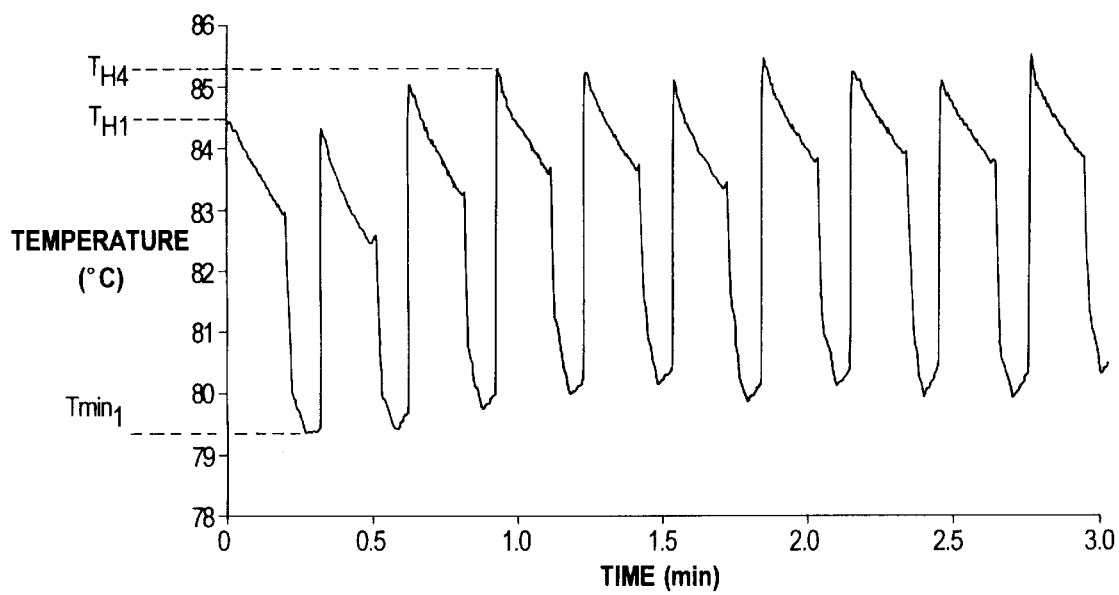

In FIG. 6, the dwell time is 10 seconds. Here, the total time in which the water is at a temperature greater than 83 degrees is greater than the total time in which the temperature is at the cooler temperature $T_C$, but the average minimum temperature $T_{min}$ (about 80 degrees C) is cooler than the results of FIG. 5.

Figure 7:
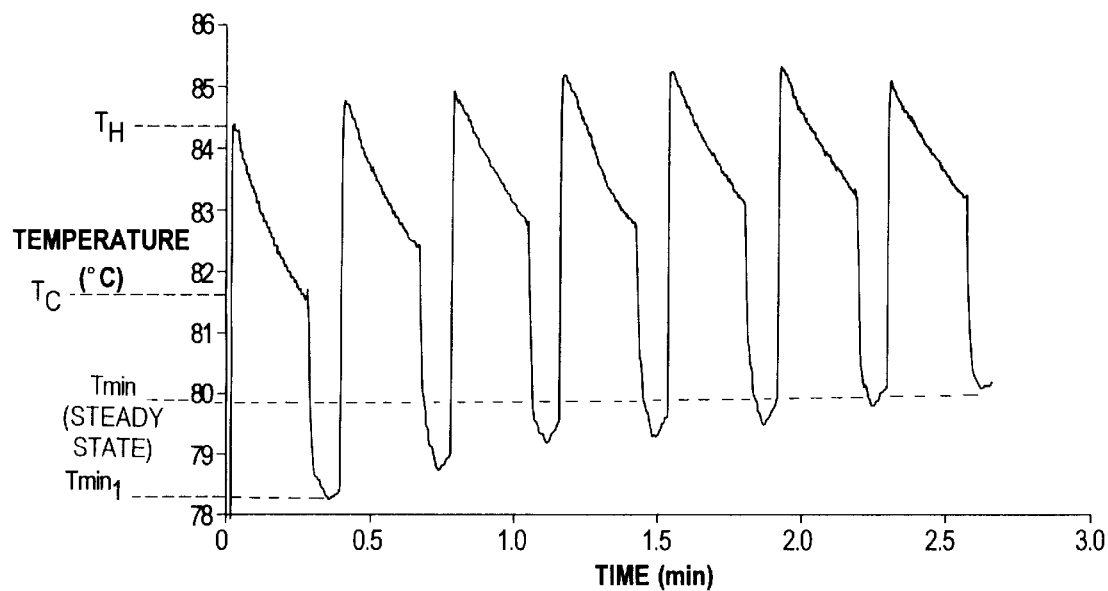

In FIG. 7, the dwell time is 15 seconds. Here, we see a greater decay in the temperature from the high temperature $T_H$ during the 15 second dwell period, as indicated at 50, with the temperature in the line reaching approximately 83 degrees ($T_C$) before it drops precipitously when the water is withdrawn from the line.

Figure 8:
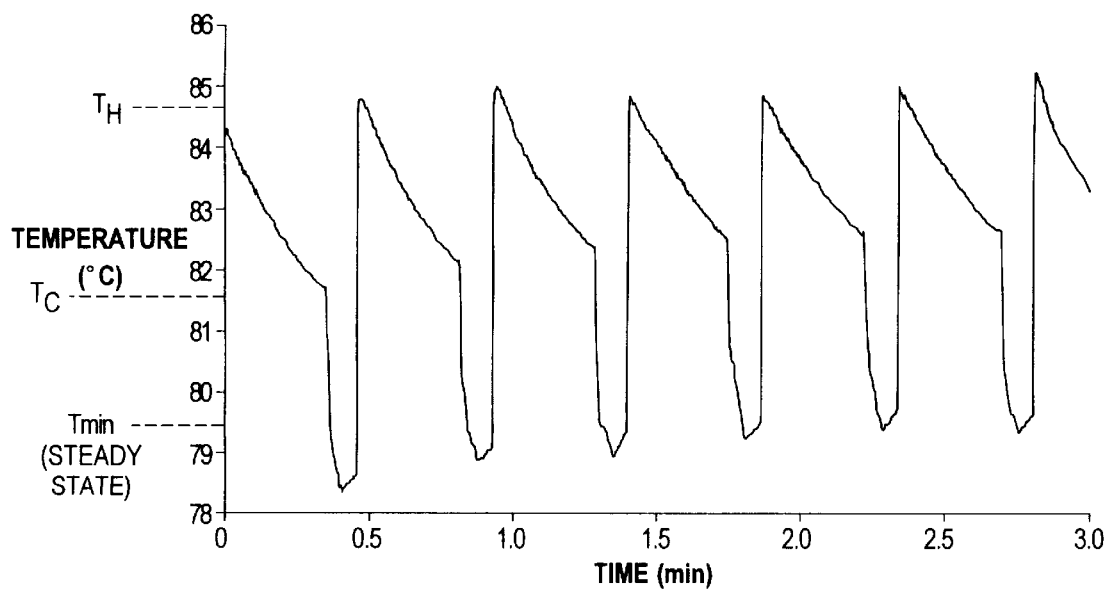

In FIG. 8, the dwell period has increased to 20 seconds. Note that the steady state minimum temperature $T_{min}$ in the example of FIG. 8 is below 80 degrees.

In FIG. 9, the dwell period is 30 seconds. By the time the water is withdrawn at the end of the dwell period it has cooled to roughly 81.5 degrees C. The minimum temperature is below 79 degrees C.

From all of the data in FIGS. 3–9, the optimum dwell time δ is selected experimentally depending on the criteria of choice, such as the dwell having the highest average temperature in the line. In the table of FIG. 10, it can be seen that the dwell time of 10 seconds (shown in FIG. 6) has the highest average temperature, 82.9 degrees C, therefore it is chosen as the optimal dwell period. Note further that the average difference between $T_H$ and $T_C$ for the results of FIG. 6 is less than two degrees C. Preferably this difference will be less than three degrees C. However, greater temperature difference can be tolerated if the initial temperature $T_H$ is hotter.

Figure 11:
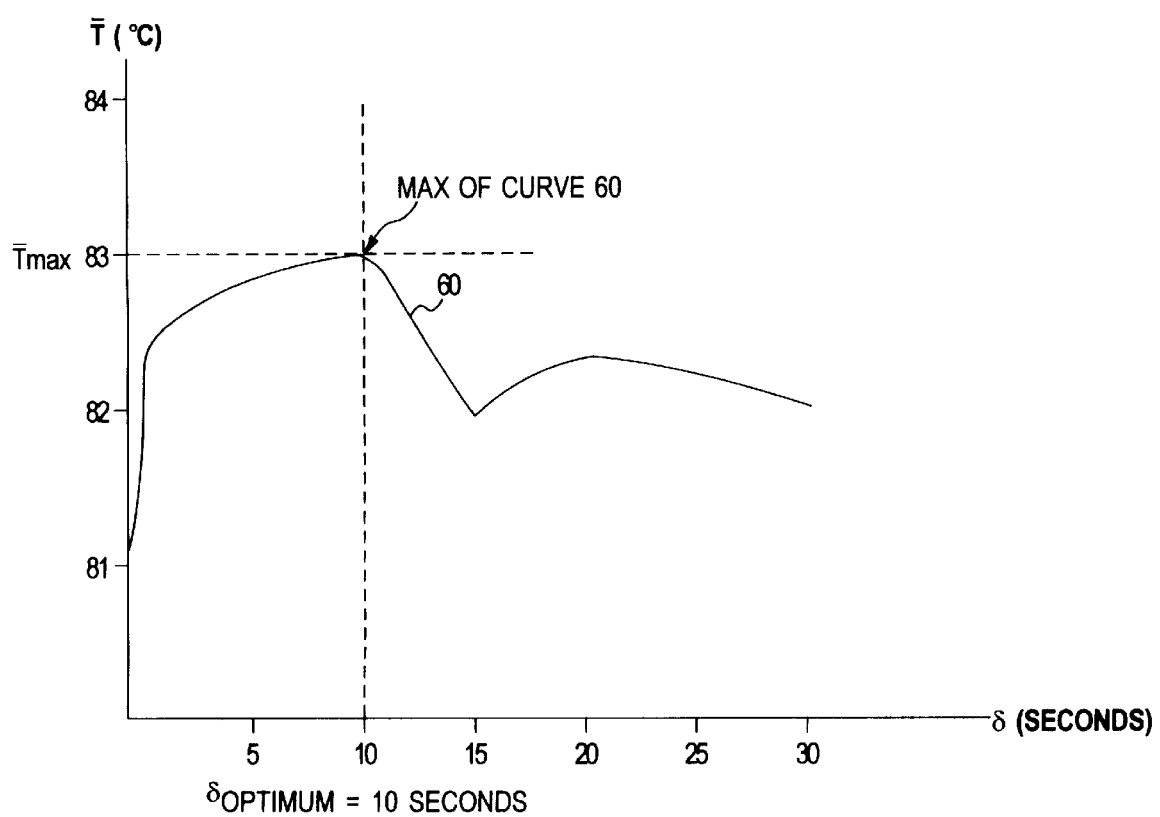
FIG. 11 is a graph of average temperature as a function of dwell time for the experimental data in FIGS. 3–9.

The results of FIG. 10 can be graphed, as shown in FIG. 11. The curve 60 of average temperature as a function of dwell time can be used to identify an optimum dwell time by finding its maximum, in the event that the optimal dwell time is between one of the data points.

In all of the data shown in FIGS. 3–9, the average temperature of the water that was being circulated through the blood tubing set and venous bubble trap of FIG. 2 was 87.1 degrees C. Thus, in order to meet a particular average temperature objective in the dead-ended line in question, the temperature of the source of water may need to be raised from what it would ordinarily be in order to account for heat loss in the dead-ended line. Furthermore, all temperature readings in FIGS. 3–9 were made at the end of the line (furthest away from the source of hot water) where the temperature would be expected to be the coolest.

In a preferred embodiment, the difference in temperature between $T_H$ and $T_C$ is less than about 3 degrees C and the dwell time δ comprises a period of between about 5 and 15 seconds. However, the experimental data for any given line may indicate a different dwell time or initial temperature $T_H$.

It will thus be appreciated that we have described a method of disinfecting a dead-ended fluid line in a medical instrument. The method comprises the steps of:

1) experimentally determining the optimum dwell time δ for a fluid heated to a high level disinfection temperature $T_H$. The dwell time comprises a period of time in which the fluid remains in the dead-ended fluid line before being removed, and with the fluid line being subsequently replenished with fluid heated to the high level disinfection temperature $T_H$ (see, e.g., FIGS. 3–10 and the average temperature plotted as a function of dwell period in FIG. 11); and 2) thereafter (a) introducing the fluid heated to said high level disinfection temperature $T_H$ into the fluid line, (b) allowing the fluid to remain in the fluid line for the optimum dwell time δ, during which the fluid cools from the temperature $T_H$ to a cooler temperature $T_C$ (see e.g., FIG. 6) and (c) removing the fluid from the fluid line, and repeating steps (a), (b) and (c) in a series of cycles until the fluid line has been disinfected.

The concept of cyclical operation of filling, dwell and flushing as recited above can be used for cleaning and rinsing of a dead-ended fluid line. For example, a dead-ended fluid line in a medical instrument, such as a dialysis machine can be cleaned and rinsed by performing the following steps:

(a) filling the fluid line with a fluid (such as water, a chemical cleaning and disinfection solution, a dialysate solution, a citric acid solution or otherwise);

(b) allowing the fluid to remain in said fluid line for a dwell time δ, (c) removing the fluid from the fluid line after the dwell time δ has elapsed, and (d) repeating steps (a), (b) and (c) in a series of cycles for a time period sufficient to achieve a cleaning and rinsing of the fluid line.

The dwell time δ may comprise a short period of say than one second or zero seconds, that is when the line is first filled the withdrawal of the fluid immediately commences. On the other hand, some longer dwell time may be appropriate to allow for dissolution of the matter retained in the line into the fluid. The optimum dwell time for cleaning and rinsing can be determined experimentally by repeating an experiment with different dwell times and determining which dwell produces the most amount of cleaning in a given time, which dwell produces the fastest cleaning to a given level of a cleaning, etc. A dwell time of between 1 and 10 seconds may be appropriate for many embodiments, but for situations where more dwell time is needed to effect a dissolution, the optimum dwell time may be greater than 10 seconds.

Persons skilled in the art will appreciate that variations to the preferred implementation, choice of fluid, dwell time, and disinfection temperature can be made without departure from the scope of the invention. The chosen level of disinfection is somewhat arbitrary from the standpoint of the patient, since other applications may require lower or higher levels of disinfection and sterilization and this has no impact on the inventive technique and concept. Hence, the claims refer to merely "disinfection", and this term should be interpreted to mean whatever level of disinfection is appropriate for the particular application of the invention and can be low, medium or high level, or even sterilization for that matter. Furthermore, the techniques described herein can be used to experimentally determine the optimum disinfection cycle for a given dead-ended line in a medical instrument. This true scope and spirit of the invention is defined by the appended claims, to be interpreted in light of the foregoing specification.

What is claimed is:

1. A method of achieving a disinfection of a dead-ended fluid line in a medical instrument, comprising the steps of:

(a) filling said fluid line with a fluid heated to a disinfection temperature $T_H$;

(b) allowing said fluid to remain in said fluid line for a dwell time δ, during which the temperature of said fluid decreases from said temperature $T_H$ to a cooler temperature $T_C$;

(c) removing said fluid from said fluid line after said dwell time δ has elapsed to thereby substantially empty said fluid line, (d) repeating steps (a), (b) and (c) in a series of cycles for a time period sufficient to achieve said disinfection of said fluid line.

2. The method of claim 1, wherein said fluid comprises water.

3. The method of claim 1, wherein said fluid comprises a citric acid solution.

4. The method of claim 1, wherein said medical instrument comprises a dialysis machine.

5. The method of claim 4, wherein said dialysis machine comprises an extracorporeal blood circuit, and wherein said fluid line comprises a vent line in a bubble trap in said extracorporeal circuit.

6. The method of claim 1, wherein said dwell time δ is less than 20 seconds.

7. The method of claim 1, wherein said dwell time δ is between 5 and 15 seconds.

8. The method of claim 1, wherein said dwell time δ is selected experimentally for said fluid line such that the difference in temperature between $T_H$ and $T_C$ is less than about 3 degrees C.

9. The method of claim 1, wherein said temperature $T_H$ is between 80 and 87 degrees C.

10. The method of claim 1, wherein the difference in temperature between $T_H$ and $T_C$ is less than about 3 degrees C and wherein said dwell time δ comprises a period of between 5 and 15 seconds.

11. A method of disinfecting a dead-ended fluid line in a medical instrument, comprising the steps:

experimentally determining the optimum dwell time δ for a fluid heated to a disinfection temperature $T_H$, said dwell time comprising a period of time in which said fluid remains in said dead-ended fluid line before being removed and with said fluid line being subsequently replenished with fluid heated to said disinfection temperature $T_H$; and thereafter (a) introducing said fluid heated to said disinfection temperature $T_H$ into said fluid line, (b) allowing said fluid to remain in said fluid line for said optimum dwell time δ during which said fluid cools from said disinfection temperature $T_H$ to a cooler temperature $T_C$, and (c) removing said fluid from said fluid line to thereby substantially empty said fluid line, and repeating steps (a), (b) and (c) in a series of cycles until said fluid line has been disinfected by said fluid.

12. The method of claim 11, wherein said fluid comprises water.

13. The method of claim 11, wherein said fluid comprises a citric acid solution.

14. The method of claim 11, wherein said medical instrument comprises a dialysis machine.

15. The method of claim 14, wherein said dialysis machine comprises an extracorporeal blood circuit, and wherein said fluid line comprises a vent line in a bubble trap in said extracorporeal circuit.

16. The method of claim 11, wherein said dwell time δ is less than 20 seconds.

17. The method of claim 11, wherein said dwell time δ is between 5 and 15 seconds.

18. The method of claim 11, wherein said dwell time δ is selected such that the difference in temperature between $T_H$ and $T_C$ is less than about 3 degrees C.

19. The method of claim 11, wherein said temperature $T_H$ is between 80 and 87 degrees C.

20. The method of claim 11, wherein the difference in temperature between $T_H$ and $T_C$ is less than about 3 degrees C and wherein said dwell time δ comprises a period of between 5 and 15 seconds.

21. The method of claim 11, wherein said dwell time δ is selected such that the average temperature in said line during said series of cycles is maximized.

22. The method of claim 11, wherein said step of experimentally determining the optimal dwell time comprises the steps of (1) circulating water heated to said disinfection temperature $T_H$ into said fluid line, (2) allowing it to remain in said line for a first dwell period, (3) measuring the temperature in said fluid line, and (4) withdrawing said fluid from said line, repeating steps (1)–(4) a plurality of times, each time having a different dwell period; and determining said optimum dwell time δ for said fluid line based on said measurements of temperature in said fluid line.

23. A method of cleaning and rinsing a dead-ended fluid line in a medical instrument comprising the steps of:

(a) filling said fluid line with a cleaning and rinsing fluid;

(b) allowing said cleaning and rinsing fluid to remain in said fluid line for a dwell time δ, (c) removing said cleaning and rinsing fluid from said fluid line after said dwell time δ has elapsed to thereby substantially empty said fluid line, and (d) repeating steps (a), (b) and (c) in a series of cycles for a time period sufficient to achieve a cleaning and rinsing of the fluid line, wherein said dwell time δ comprises less than one second.

24. A method of cleaning and rinsing a dead-ended fluid line in a medical instrument, comprising the steps:

experimentally determining the optimum dwell time δ comprising a period of time in which a cleaning and rinsing fluid remains in said dead-ended fluid line before begin, removed and with said fluid line being subsequently replenished with said cleaning and rinsing fluid; and thereafter (a) introducing said cleaning and rinsing fluid into said fluid line, (b) allowing said cleaning and rinsing fluid to remain in said fluid line for said optimum dwell time δ; and (c) removing said cleaning and rinsing fluid from said fluid line to thereby substantially empty said fluid line, and repeating steps (a), (b) and (c) in a series of cycles until said fluid line has been cleaned and rinsed;

wherein said fluid comprises water.

25. A method of cleaning and rinsing a dead-ended fluid line in a medical instrument, comprising the steps:

experimentally determining the optimum dwell time δ comprising a period of time in which a cleaning and rinsing fluid remains in said dead-ended fluid line before being removed and with said fluid line being subsequently replenished with said cleaning and rinsing fluid; and thereafter (a) introducing said cleaning and rinsing fluid into said fluid line, (b) allowing said cleaning and rinsing fluid to remain in said fluid line for said optimum dwell time δ; and (c) removing said cleaning and rinsing fluid from said fluid line to thereby substantially empty said fluid line, and repeating steps (a), (b) and (c) in a series of cycles until said fluid line has been cleaned and rinsed;

wherein said optimal dwell time is between 1 and 10 seconds.

* * * * *